(12) United States Patent
Kurian et al.

(10) Patent No.: US 7,805,397 B2
(45) Date of Patent: Sep. 28, 2010

(54) INTELLIGENT DATA MANAGEMENT SYSTEM AND METHOD

(75) Inventors: Joseph C. Kurian, North York (CA); Hue Tran, North York (CA); William Melek, Toronto (CA); Homayoun Najjaran, Kelowna (CA); Afshan Zahedi, Richmond Hill (CA); Saeed Ziaee, Richmond Hill (CA)

(73) Assignee: Alphaglobal IT Inc., North York (CA)

( * ) Notice: Subject to any disclaimer, the term of this patent is extended or adjusted under 35 U.S.C. 154(b) by 37 days.

(21) Appl. No.: 12/272,502

(22) Filed: Nov. 17, 2008

(65) Prior Publication Data

US 2009/0070149 A1    Mar. 12, 2009

Related U.S. Application Data

(63) Continuation of application No. 10/533,872, filed as application No. PCT/CA03/01686 on Nov. 3, 2003, now abandoned.

(30) Foreign Application Priority Data

Nov. 5, 2002    (CA) .................................... 2411203

(51) Int. Cl.
*G06F 9/44*  (2006.01)
*G06N 7/02*  (2006.01)
*G06N 7/06*  (2006.01)

(52) U.S. Cl. ...................................... 706/52

(58) Field of Classification Search ................... 706/52
See application file for complete search history.

(56) References Cited

U.S. PATENT DOCUMENTS

| 5,672,154 | A | | 9/1997 | Sillen et al. |
|---|---|---|---|---|
| 5,687,290 | A | | 11/1997 | Lewis |
| 5,787,407 | A | | 7/1998 | Viot |
| 5,809,493 | A | | 9/1998 | Ahamed et al. |
| 6,157,935 | A | * | 12/2000 | Tran et al. ................... 715/202 |
| 6,202,060 | B1 | * | 3/2001 | Tran .................................. 1/1 |
| 6,272,481 | B1 | * | 8/2001 | Lawrence et al. ............. 706/45 |
| 2002/0107824 | A1 | | 8/2002 | Ahmed |

OTHER PUBLICATIONS

The Effect of Fuzzy Logic on Database, Abadi, M.R.D.M.; Samavarchi, H.; Computer Science and Information Engineering, 2009 WRI World Congress on vol. 5 Digital Object Identifier: 10.1109/CSIE.2009.224 Publication Year: 2009, pp. 712-717.*

(Continued)

*Primary Examiner*—Michael Holmes
(74) *Attorney, Agent, or Firm*—Pearne & Gordon LLP (57) ABSTRACT

An intelligent data management system and method are disclosed. The system includes a database of stored data, a middleware layer having access to the stored data, and at least one client device for remotely accessing a provided course of action. The middleware layer includes a fuzzy logic knowledge base for generating, updating, or firing fuzzy logic rules and a fuzzy logic inference engine for processing the stored data guided by the fuzzy logic rules to provide the course of action.

31 Claims, 4 Drawing Sheets

OTHER PUBLICATIONS

A Mechanism for Efficient Management of Changes in BPEL based Business Processes: An Algebraic Methodology, Jeewani A. Ginige; Uma Sirinivasan; Athula Ginige; e-Business Engineering, 2006. ICEBE '06. IEEE International Conference on Digital Object Identifier: 10.1109/ICEBE.2006.7 Publication Year: 2006, pp. 171-178.*

Fuzzy partition models and their effect in continuous speech recognition, Kato, Y.; Sugiyama, M.; Neural Networks for Signal Processing [1992] II., Proceedings of the 1992 IEEE-SP Workshop Digital Object Identifier: 10.1109/NNSP.1992.253702 Publication Year: 1992, pp. 111-120.*

Computing With Words Is an Implementable Paradigm: Fuzzy Queries, Linguistic Data Summaries, and Natural-Language Generation, Kacprzyk, J.; ZadroÅ¿ny, S.; Fuzzy Systems, IEEE Transactions on vol. 18, Issue: 3 Digital Object Identifier: 10.1109/TFUZZ.2010.2040480 Publication Year: 2010, pp. 461-472.*

Spahni S et al: "Towards specialised middleware for healthcare information systems" International Journal of Medical Informatics, Elsevier Scientific Publishers, Shannon, IR, vol. 53, No. 2-3, Feb. 3, 1999, pp. 193-201, XP004162196 ISSN: 1386-5056 abstract; figure 3.

* cited by examiner

INTELLIGENT DATA MANAGEMENT SYSTEM AND METHOD

FIELD OF THE INVENTION

The present invention relates generally to electronic databases, and more particularly to a data management system and method.

BACKGROUND OF THE INVENTION

Today, faced with an increasingly mobile population, global accessibility to healthcare information is becoming increasingly essential. Unfortunately, early electronic approaches to automated medical record systems tended to apply industrial engineering concepts to understanding and automating the flow of healthcare data, with the expectant failures.

It has been envisioned that the future patient record will be that of a multimedia record capable of including text, high-resolution images, sound, and full-motion video. These systems, which have come to be known as Computer-Based Patient Record (CPR) systems, will ultimately be expected to offer improved access, quality, security, flexibility, connectivity, and efficiency.

CPR systems are used to maintain patient records such as histories, reports, charts, and images in digitized form within the networked system of one or more health care institutions. This enables authorized users to access patient records remotely employing client devices such as desktop computers, laptops, personal digital assistants (PDA's) and the like, coupled to a networked system via wired and/or wireless network paths.

Today, knowledge bases provide machine-readable resources for the dissemination of information, generally online or with the capacity to be put online. An integral component of knowledge management systems, a knowledge base is used to optimize information collection, organization, and retrieval for an organization, or for the public at large. A well-organized knowledge base can save an enterprise a considerable amount of money by decreasing the amount of employee time spent trying to find information about such topics as tax laws, or company policies and procedures. A knowledge base can give users easy access to information that would otherwise require laborious contact with many people.

In general, a knowledge base is not a static collection of information, but a dynamic resource that can itself have the capacity to "learn", as part of an artificial intelligence (AI) expert system for example. An expert system is a computer application that performs a task that would otherwise be performed by a human expert. For example, there are expert systems that can make financial forecasts or schedule routes for delivery vehicles. Some expert systems are designed to take the place of human experts, while others are designed to aid them. To design an expert system, a knowledge engineer studies how human experts in a particular field make decisions. They then create rules that are subsequently translated into terms a computer can understand.

However, existing knowledge bases are so inherently tied to their inference engines that they lack flexibility. Typically, within a knowledge base, the tool of choice has been the "IF_THEN" conditional statement. A basic IF-THEN statement is used when the choice is whether to take an action or not; there is no alternative action. The condition in an IF-THEN statement is considered true if its value is non-zero, and false if its value is zero. The IF-THEN statement provides direction only when a parameter is found to be true. The problem is that IF-THEN statements are too rigid. What is needed is a data management system that can better emulate the superior reasoning processes of a human to facilitate diagnosis and treatment in an efficient and effective manner.

For the foregoing reasons, there is a need for an improved system and method for the management of medical and other records.

SUMMARY OF THE INVENTION

The present invention is directed to an intelligent data management system and method. The system includes a database of stored data, a middleware layer having access to the stored data, and at least one client device for remotely accessing a provided course of action. The middleware layer includes a fuzzy logic knowledge base for generating, updating, or firing fuzzy logic rules and a fuzzy logic inference engine for processing the stored data guided by the fuzzy logic rules to provide the course of action.

In an aspect of the present invention, the system further includes a gateway to facilitate wireless access to the middleware layer from a client device leveraging existing wireless networks. In an aspect of the present invention, the system further includes a load balancer for balancing loads between the client device and the middleware layer.

The method includes the steps of accessing stored data, providing a course of action using the accessed data, and remotely accessing the provided course of action. The step of providing a course of action further includes the steps of generating, updating, or firing fuzzy logic rules and processing the stored data using fuzzy logic inference guided by the fuzzy logic rules.

By generating fuzzy rules for capturing expert knowledge, rules can be later updated based on feedback from the system, and without having to change the inference engine programming code. By using hand-held client devices, the system provides mobile data management for medical care units, and enables efficiencies in patient treatment, cost efficiencies, paper-work reduction, resource allocation and utilization management, error minimization, and clinical research and data mining capabilities.

By providing an intelligent system capable of assisting in accurate diagnosis and treatment, the system provides timely information through the use of a wireless hand-held client device to cost-effectively deliver global accessibility to patient records. The system further provides near real-time information to aid in the making of clinical decisions, and streamlines the clinical process to improve decision-making quality to facilitate medical procedures, speed up processing times, and eliminate paper-related errors.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE PRESENTLY PREFERRED EMBODIMENT

Figure 1:
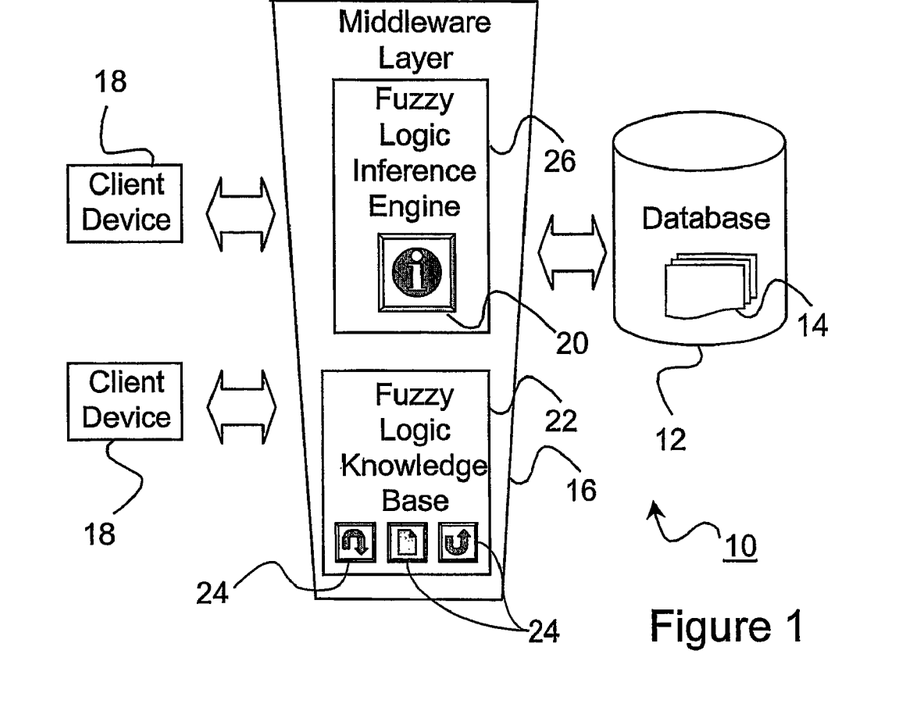
FIG. 1 is an overview of an intelligent data management system in accordance with an embodiment of the present invention.

The present invention is directed to an intelligent data management system and method. As illustrated in FIG. 1, the system 10 includes a database 12 of stored data 14, a middleware layer 16 having access to the stored data 14, and at least one client device 18 for remotely accessing a provided course of action 20. The middleware layer 16 includes a fuzzy logic knowledge base 22 for generating, updating, or firing fuzzy logic rules 24 and a fuzzy logic inference engine 26 for processing the stored data 14 guided by the fuzzy logic rules 24 to provide the course of action 20.

Figure 3:
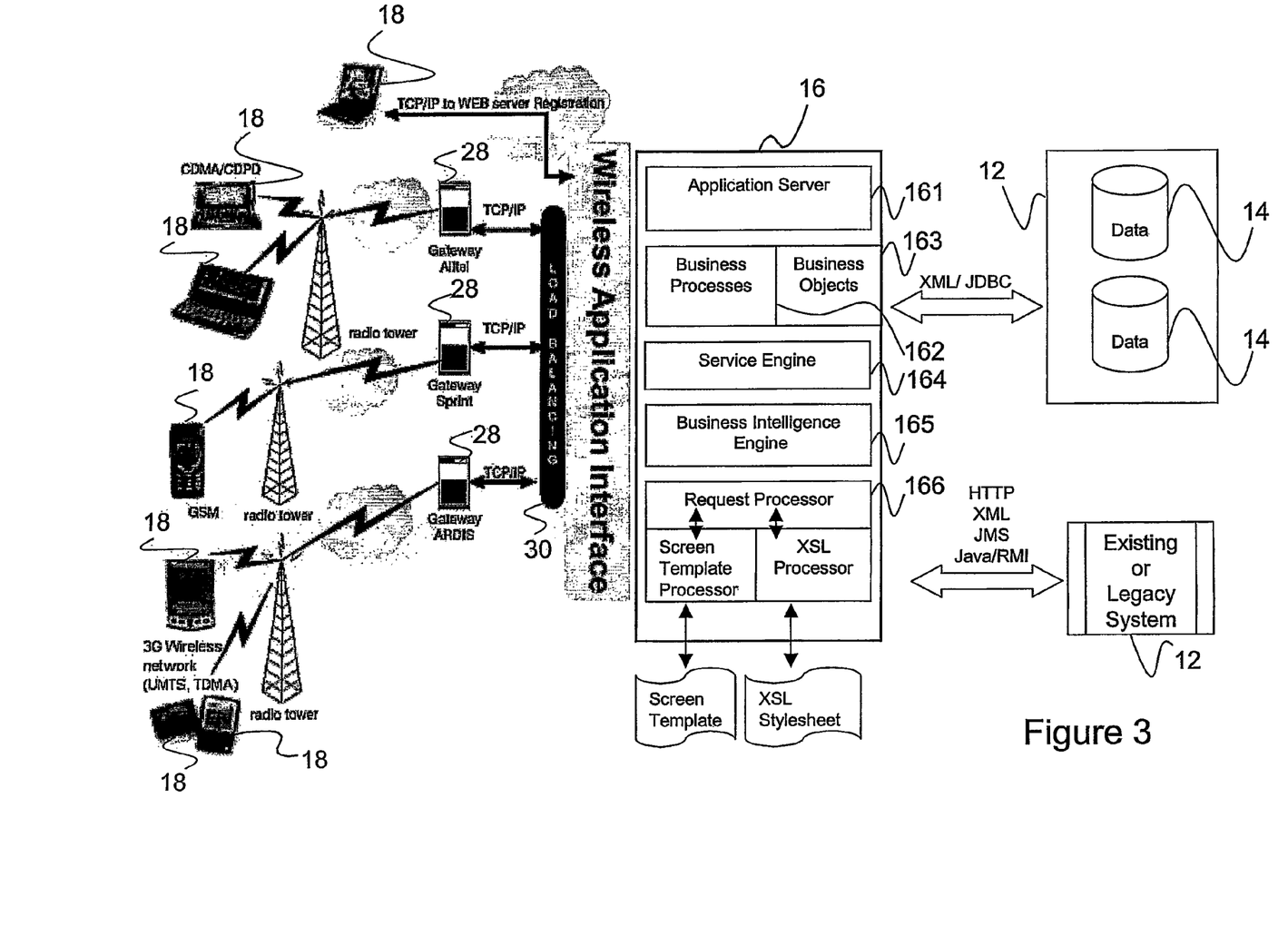
FIG. 3 illustrates an overview of a wireless architecture in accordance with an embodiment of the present invention.

In an embodiment of the present invention, as illustrated in FIG. 3, the system 10 further includes a gateway 28 to facilitate wireless access to the middleware layer 16 from a client device 18 leveraging existing wireless networks. In an embodiment of the present invention, the system 10 further includes a load balancer 30 for balancing loads between the client device 18 and the middleware layer 16.

Figure 2:
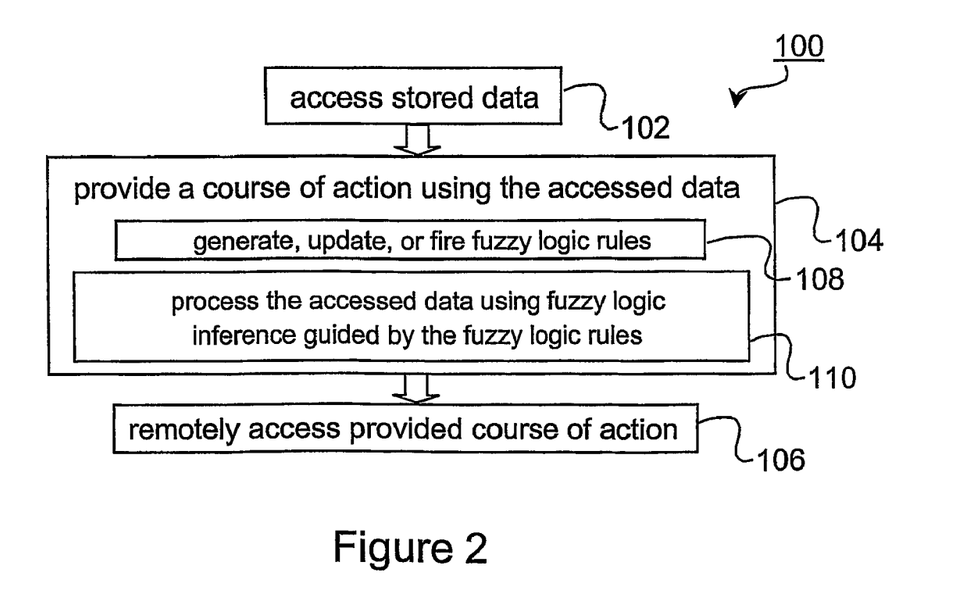
FIG. 2 is an overview of an intelligent data management method in accordance with an embodiment of the present invention.

As illustrated in FIG. 2, the method 100 includes the steps of accessing stored data 102, providing a course of action using the accessed data 104, and remotely accessing the provided course of action 106. The step of providing a course of action 104 further includes the steps of generating, updating, or firing fuzzy logic rules 108 and processing the stored data using fuzzy logic inference guided by the fuzzy logic rules 110.

The following described embodiments are directed to medical record management embodiments, provided as exemplary examples of the present invention. Although what is described herein is directed to medical record management embodiments, it should be noted that other embodiments are contemplated and envisioned such as, but not limited to, materiel handling systems, transportation systems, and governmental services.

The system 10 is provided in a flexible object model to provide analysis and design of patient charts, as well as billing and scheduling capabilities. The database 12 is a patient-based design with data 14 categorized and stored based on its importance in diagnosis. An object-oriented analysis provides an effective approach for communicating with the application and domain expert.

Figure 4:
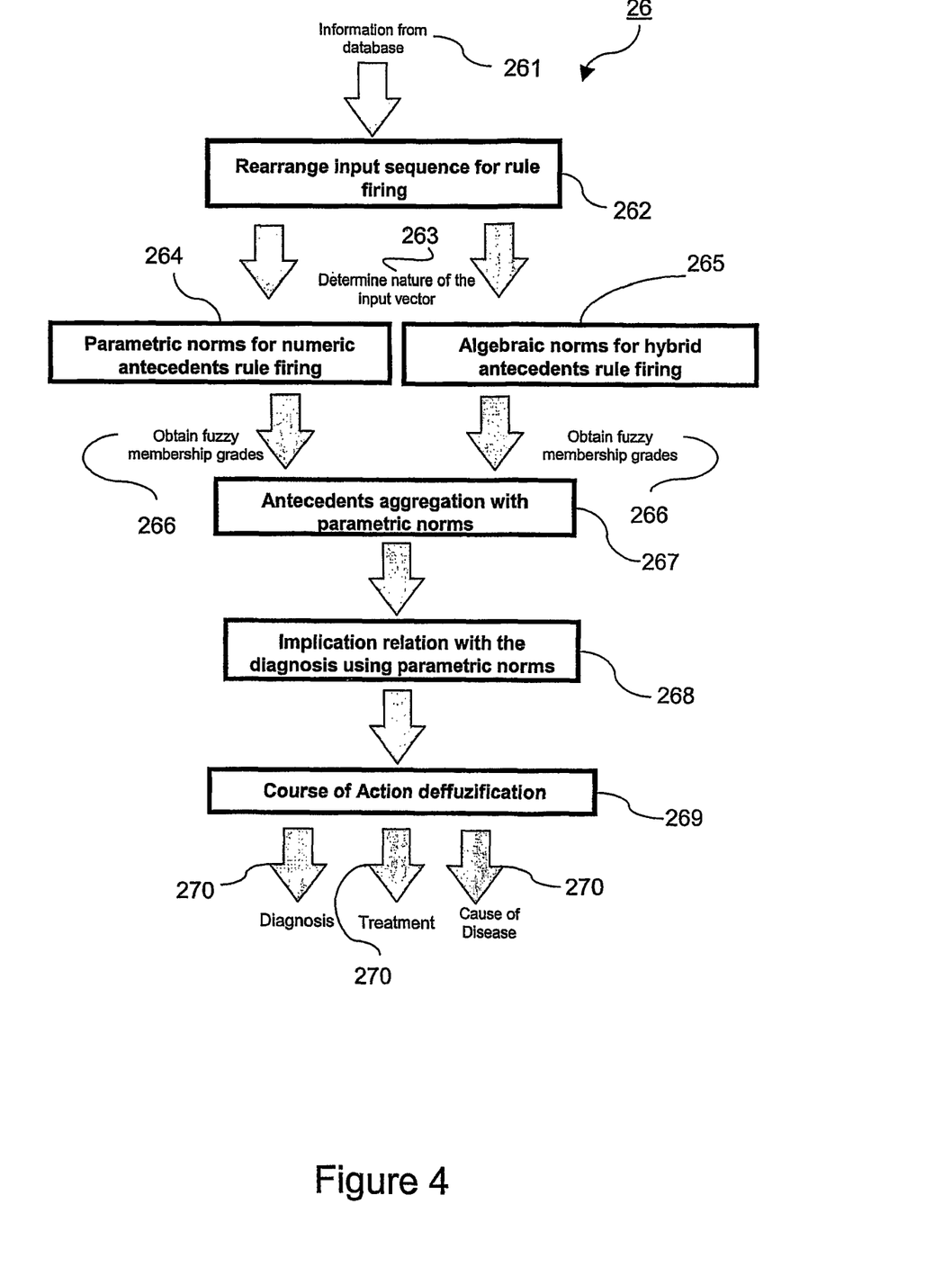
FIG. 4 illustrates a fuzzy inference engine structure flowchart.
Figure 5:
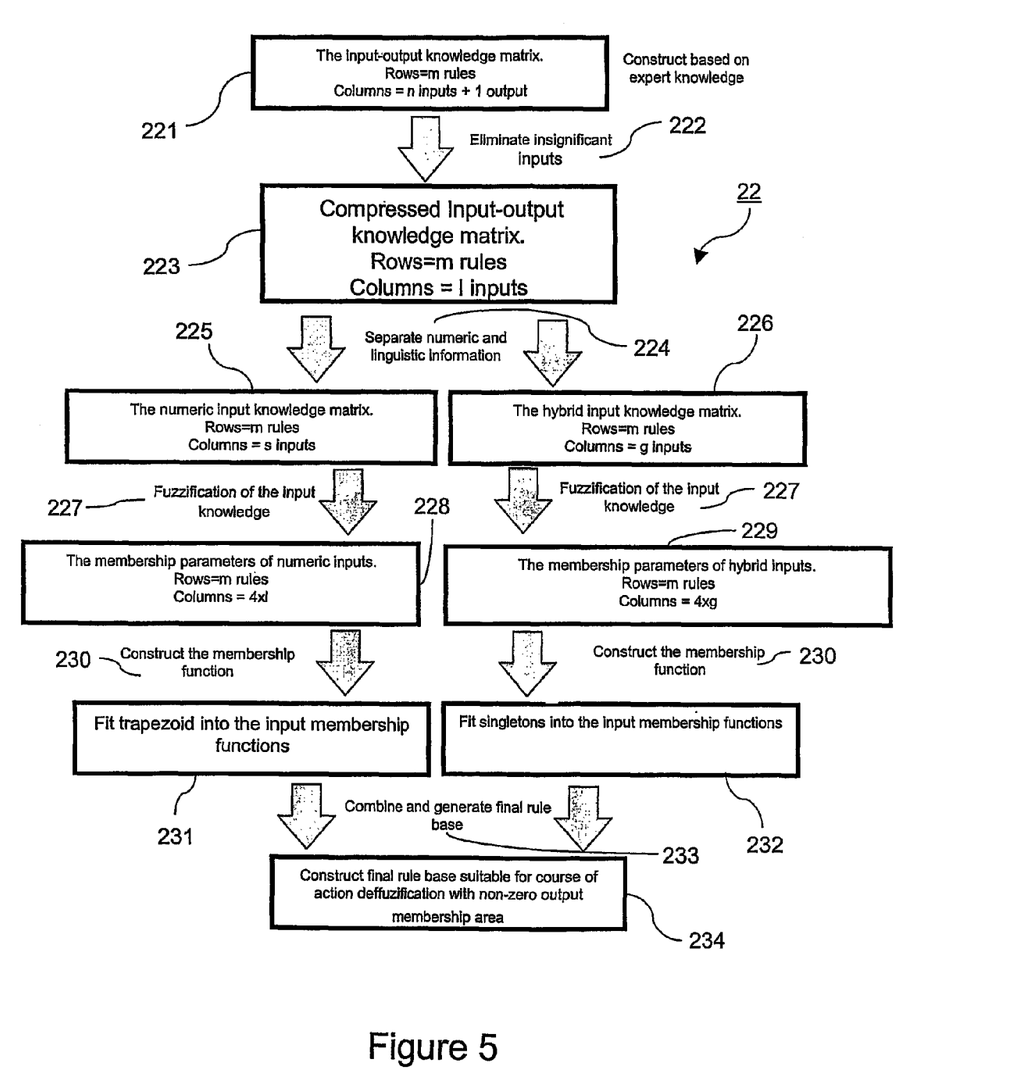
FIG. 5 illustrates a fuzzy knowledge base structure flowchart.

As illustrated in FIG. 4, the fuzzy logic inference engine 26 provides the decision-making capacity. The fuzzy logic inference engine 26 has been designed and implemented for medical diagnosis purposes. However, since the engine is modular, it can be restructured for other uses. As illustrated in FIG. 5, the system 10 leverages expert knowledge to create a knowledge base 22 and fuzzy logic rules 24 to capture this knowledge and be available for process by the independent fuzzy inference engine 26. By creating a modular inference engine 26 that is separate from the knowledge base 22, updating the diagnosis and treatment rules 24 is made easier.

The modular inference engine 26 is parameterized with various indices that help cover a wide variety of inference mechanisms between the Mamdani and Formal Logical extremes. A precise diagnosis is computed through a parameterized defuzzification method with parametric norms used for rule firing using information obtained from the fuzzy rules 14. The parameterized inference engine 26 provides the flexibility to adapt to one of many possible methods of reasoning, some of which can perform better than others in the diagnosis of a specific disease within a medical discipline.

The inference engine 26, as a class entitled 'InferenceEngine', has been designed to include the database 12 and procedures required for diagnosis, cause and treatment of medical conditions. The class retrieves patient information from the database 12 through 'GetFactor' functions, and launches a fuzzy logic procedure for diagnosis. The system 10 provides guidance for experts on how to structure their knowledge for rule generation.! As illustrated in Table 1, the fuzzy logic inference engine is modular with multiple operators.

TABLE 1

| Fuzzy Logic Inference Engine Operators | |
|---|---|
| Fuzzy numbers: | |
| Creat | Create a fuzzy number in two steps |
| GetFiredHeight | Find the height of a fuzzy number to the effect of an event |
| GetMin | Find the minimum range of a fuzzy number |
| GetMax | Find the maximum range of a fuzzy number |
| GetArea | Find the area of a fuzzy number |
| Rule Base: | |
| SNorm | Obtain the summation of all fired fuzzy numbers |
| TNorm | Find the interaction of the fuzzy numbers |
| Defuzzify | A generic defuzzification method that uses a parameter to determine the defuzzification method used |
| DoProcess | Perform the diagnosis process |
| Inference | Perform the fuzzy inference |
| GetDrawPoint | Only for displaying the result |

Knowledge structuring can include a list of diagnosis and/or lab tests, family histories, medical examinations, as well as medical procedures related to diagnosis. In addition, knowledge structuring can further include defining relationships, logical expression of relationships, choosing keywords for processing, prioritizing of all related parameters to diagnosis, sensitivity analyzing, and classifying parameters.

For handling numeric and linguistic inputs, a rule base is constructed to provide a suitable course of action 20 through "defuzzification", with a non-zero output membership area. An object-oriented approach has been used in designing the database 12 structure. The database 12 gathers patient related data 14 and stores it in several main categories such as Personal Information, Lab Test, Diagnostic Imaging, Report, Medical History Physical Examination, Surgical Pathology and Diagnosis categories.

In an embodiment of the present invention, data 14 from a patient's medical records can be utilized by a billing component to better automate the system 10, and to provide cost savings through the elimination of data entry overlap. This provides a flexible billing system that meets the diverse requirements of a variety of providers, and can further include a laboratory central pool, a pharmacy central pool, and/or a material central pool.

In an embodiment of the present invention, the system 10 is implemented at least in part as a wireless solution. While the system 10 can be run from standalone computer platforms, the system 10 is advantageously utilized within a wireless network environment to take advantage of the power and flexibility inherent within the system 10. Medical personnel can then carry hand-held devices that provide them with real time access to a patient's medical records instead of the limited and cumbersome traditional methods of carrying paper folders, clipboards, and the like.

FIG. 3 illustrates a wireless architecture overview in accordance with an embodiment of the present invention. The system 10 provides a flexible architecture designed to support wireless handheld client devices 18. All information relating to patients can be stored on a server with a handheld device 18 used to retrieve the information from the server leveraging the wireless infrastructure. Multiple wireless access points can be provided to ensure connectivity throughout an entire medical unit. All diagnostic images, prescriptions, laboratory results and treatment information are then stored on a server and can be retrieved through the handheld client device 18.

In general, the architecture is divided into 3 layers, the client device 18 layer, the middleware layer 16, and the database 12 layer. The client device 18 layer can be an application client, web client, or wireless handheld client device. The middleware layer 16 contains all business rules, business objects and entities, and any supporting services such as security, reports, and queries. Thirdly, the database 12 layer is where all data 14 is stored, and normally where the database 12 resides. With this flexible architecture, the system 10 can support wireless applications with less effort because all rules, entities, and services reside in the middleware layer 16 and not within the database 12. Therefore, developers need only concentrate on developing communications between the wireless handheld client device 18 and the middleware layer 16, presenting information to the handheld client devices 18, and supporting databases in the handheld client devices 18.

The system's architecture includes a wireless client device 18, such as a smart phone, handheld devices, pocket PC, and the like, which communicates through a wireless network such as CDMA (Code Division Multiple Access), CDPD (Cellular Digital Packet Data) or GSM (Global System for Mobile communication) to a gateway 28. The gateway 28 then communicates with the middleware layer 16 through TCP/IP (Transmission Control Protocol/Internet Protocol). The middleware layer 16 then manipulates the data 14 in the data 14 layer and communicates with any legacy systems using protocols such as JDBC (Java Data Base Connectivity), JMS (Java Messaging Services), XML (extensible Markup Language), and HTTP (Hyper Text Transfer Protocol). The system's wireless architecture is capable of handling a variety of wireless communications such as batch transfers from server to hand-held device, real-time transfers from server to hand-held device, and real-time transfers between hand-held devices.

Because the system 10 uses a standard XML (Extensive Markup Language) or other similarly flexible markup language to exchange and structure information, it can support both wired clients and wireless clients. By using XML language, the system 10 can use XSL (Extensible Stylesheet Language) to transform the data 14 into different formats or different presentations. For example, if a web client makes a request using the HTTP protocol, then the system 10 transforms the XML into HTML (Hyper Text Markup Language) using XSL before responding to the client 18. However, if a wireless handheld client device 18 makes a request using WAP (Wireless Application Protocol), then the system 10 transforms the XML into WML (Wireless Markup Language) using XSL before passing the response back to the client 18. Such a flexible architecture is needed in order to handle different types of wireless handheld client devices 18 using different markup languages for content delivery. The application server 161 can readily be used as a wireless application server. In addition, the system 10 can support Java clients, web clients, and/or wireless clients.

The system 10 architecture utilizes J2EE (Java 2 Enterprise Edition) technology, a widely adopted technology for building enterprise applications. Since the system 10 is based on a flexible architecture technology, it can be deployed on virtually any platform. J2EE technology includes elements such as EJB (Enterprise Java Bean(s)), JSP (Java Server Pages)/Servlet, JDBC, JMS, Java mail, and JNDI (Java Naming and Directory Interface). The application server 161 can be configured for use as a wireless application server 161. As discussed previously, XML is used for information exchange and for structuring information. As for the handheld client device 18, the system 10 can support java clients, web clients, and/or wireless clients.

As well, the system 10 can support wireless applications including wireless web, lightweight database, and thin client/server applications. The wireless web technology is provided as a browser technology. For this type of wireless application, the system 10 supports WML/WAP. The system 10 architecture makes it flexible enough to support all major mark-up languages for wireless devices.

In this architecture, the client device 18 is used only for presenting information. All business logic resides in the middleware layer 16. As illustrated in FIG. 3, the middleware layer 16 includes the application server 161, business process 162, business entities 163, application services 164, business intelligence module 165, and request processor 166. The application server 161 manages transactions, resources, and persistent data 14. The business process 162 is where all business rules and logics reside. The purpose of the business process 162 is to process the information within the business objects, which encapsulates the business information. The advantage of separating business processes from business objects is that business objects are then reusable entities that can be reused within other applications. This provides great advantages since business objects are seldom changed, while on the other hand business rules and processes are constantly changing.

The application services 164 are services that support the business such as security services, query services, report services, and messaging services. The business intelligence module 165 is an artificial intelligence module that assists a physician or hospital in providing patient healthcare. The request processor module 166 processes requests from the client devices 18 and presents information to the client device 18. The data layer 12 includes the databases 12 where all data 14 is stored, and can further include legacy systems 121.

Wireless devices can be supported with modules such as "scheduler", "view/transfer patient chart", and "order entry" modules. Schedulers are generic and flexible, and can automatically make appointments based on available resources and the needs of a specific situation. Appointment parameters include date, time, people to meet, and/or equipment required and procedures to be performed, as well as the space required for these procedures. In order for appointments to take place in an orderly fashion, all parameters need to be scheduled to come together at a pre-selected date and timeslot for a particular appointment.

In addition, a scheduler is capable of re-adjustment if and when an appointment has to be changed. The purpose of the scheduler is to make the most efficient use of the aforementioned parameters for any appointments for which they are required. To ensure that the scheduler is generic and flexible, it has been designed to treat all appointment parameters as resources so that the scheduler can be used in other applications. For medical applications, resources include patients, providers, equipment, and locations.

The scheduler, through the use of search strategies, has the capacity to maximize the number of medical procedures performed in medical institutions such as emergency room admission, MRI imaging, X-ray, open-heart surgery, CT scans, and consultation for given a set of medical resources.

The Scheduler is also capable of maximizing the number of procedures that can be completed within a constraint time horizon through the use of active schedule generation to analyze the unavailability patterns of human and equipment resources, as well as medical personnel work hours.

In addition, the scheduler enables the efficient scheduling of available professional resources like nurses and physicians, as well as other resources like beds and emergency rooms for a given number of medical procedures that need to be completed over a fixed time span. Since this process is currently being performed manually, automating this process involves the generation of schedules that abide by the time constraints and unavailability patterns of existing hospital resources, as well as the level of dependency of a given procedure on other procedures that need to be completed concurrently or sequentially.

While this process may be constrained for a given time horizon, set of procedures, or resources available at a given medical institution, over a sufficient learning period of time, the scheduler can optimize the above criteria to re-schedule patients using the system's 10 incorporated AI (Artificial Intelligence) technology.

An AI engine has been incorporated into the scheduler that learns how a particular provider utilizes appointment times for different types of appointments, so that the scheduler is able to suggest an appropriate duration for appointments of differing types and/or providers. The scheduler's 'learned intelligence' is capable of suggesting the earliest available time slot for an appointment based on the type of appointment and resources required.

The scheduler's AI engine facilitates the efficient use of resources for various appointments and medical procedures that are required without sacrificing the capacity to prioritize appointments or procedures based on the urgency of a matter. For example, one procedure might require three resources with a procedure duration of one hour. However, the third resource may only be required ten minutes after the start of the procedure, and for just twenty minutes. The scheduler can then make that resource available for other procedures where it is required, thereby making efficient use of that resource.

The scheduler is user-customizable since it's design is based on a template and dictionary, or knowledge base. A user can create different types of appointments with different types of resources. A user can also pre-assign resources specifically required for a particular appointment as a default value in a template, such as when a specific surgeon is required or requested by a patient. Therefore, complicated appointments such as those that have "fixed resources" as default values and other resources as variables ones, which when done in the traditional manner may take a day or more to schedule, can be made in near real time.

The scheduler is capable of handling highly sophisticated and complex appointment schedules. One example of a complex appointment is that of a main appointment that depends upon several additional appointments. For example, a surgical appointment might require that the patient have a physical and X-rays taken before a surgical procedure can be performed.

As an example, a View/Transfer patient chart module will typically include patient information, the patient's history, a patient problem list, patient treatments, and patient diagnostic results such as X-Rays, MRI's, and laboratory results. An Order Entry module will typically include laboratory requisitions, prescriptions, and diagnostic procedures. Examples of patient record management tasks include the creation, editing, and updating of patient records, retrieving pertinent information and manipulating diagnostic images. Image handling can include rotation, side-by-side and overlapping comparisons.

The inclusion of a thin client/server technology enables seamless communication between the handheld client device 18 and the middleware layer 16. The handheld client device 18 can then make use of the services provided by the middleware layer 16. However, since different handheld client devices 18 have different platforms, it would be preferable that the client programming be written using J2ME (Java 2 Micro Edition), a lightweight version of Java technology, or other similarly lightweight language that targets small devices to avoid having to write client programs for every platform. Because J2ME is Java technology, it resolves the problem of security since the code can be downloaded, is platform independent, provides full-color graphics, and supports robust applications. In addition, a user can enjoy full color graphics and manipulate diagnostic images, such as X-ray images, on the hand-held device 18.

The use of lightweight databases on the handheld client devices 18 is highly desirable within healthcare applications where there often is a need to work offline, either for cost-saving reasons or for locations where no network coverage exists. With the system 10, a user is able to store information locally on a handheld client device 18 using a JDBC interface. Any changes will then be synchronized with a master database over a wireless connection when network access again becomes available. A further use for this lightweight database is for the preloading of static information such as drug formulary, making it possible for physicians to prepare prescriptions on the hand-held client device 18 before sending them to a pharmacy.

The system 10 provides an artificial intelligence engine 165 with an intelligent graphical web browser interface that facilitates decision-making in diagnosis and treatment. The deployment of mobile wireless technology facilitates the use of hand-held client devices 18 to access patient information from a central pool so that, by applying the intelligent graphical web browser interface to a database 12 of electronic medical records, critical information can be reviewed before any decision-making takes place. This not only expedites processing time, but also will ultimately eliminate paperwork and associated errors.

In addition, the system 10 incorporates elements that ensure compliance with privacy regulations or confidentiality requirements. The system 10 provides global accessibility to patient records through the use of an electronic medical record via centralized storage of patient records including diagnostic images.

By generating fuzzy rules 24 for capturing expert knowledge, rules 24 can be later updated based on feedback from the system 10, and without having to change the inference engine 26 programming code. By using hand-held client devices 18, the system 10 provides mobile data management for medical care units, and enables efficiencies in patient treatment, cost efficiencies, paper-work reduction, resource allocation and utilization management, error minimization, and clinical research and data mining capabilities.

By providing an intelligent system capable of assisting in accurate diagnosis and treatment, the system 10 provides timely information through the use of a wireless hand-held client device 18 to cost-effectively deliver global accessibility to patient records. The system 10 further provides near real-time information to aid in the making of clinical decisions, and streamlines the clinical process to improve decision-making quality to facilitate medical procedures, speed up processing times, and eliminate paper-related errors.

Although the present invention has been described in considerable detail with reference to certain preferred embodiments thereof, other versions are possible. Therefore, the spirit and scope of the appended claims should not be limited to the description of the preferred embodiments contained herein.

What is claimed is:

1. A fuzzy logic method for reasoning about data, comprising the steps of:
   (i) accessing the data;
   (ii) determining a type of the data from a group consisting of numeric, linguistic and a hybrid combination thereof;
   (iii) selecting a rule for firing based on the determined type of the data;
   (iv) obtaining fuzzy membership grades;
   (v) aggregating the fuzzy membership grades by invoking a parametric formulation;
   (vi) applying a compositional rule of inference parametrically to extract a consequent to obtain a fuzzy output; and
   (vii) defuzifying the fuzzy output.

2. The method according to claim 1, further comprising the step of aggregating the consequents from the fired rules.

3. The method according to claim 1, further comprising the step of rearranging a sequence of the data prior to the determining step.

4. The method according to claim 1, wherein the data is stored in a database.

5. The method according to claim 1, wherein the type of the data is linguistic, and wherein the rule has a singleton consequent.

6. The method according to claim 1, wherein the type of the data is hybrid, and wherein the rule has a singleton consequent.

7. The method according to claim 1, wherein the firing of the rule uses a special t-norm operator.

8. The method according to claim 1, wherein the firing of the rule uses an algebraic product norm.

9. The method according to claim 1, wherein the type of the data is numeric, wherein the firing of the rule uses a parametric t-norm.

10. The method according to claim 1, further comprising the step of interacting with a client device.

11. The method according to claim 10, wherein the client device is wireless.

12. The method according to claim 1, wherein the data is medical data.

13. A fuzzy logic expert system for reasoning about data, comprising:
   (i) means for accessing the data;
   (ii) means for determining a type of the data from a group consisting of numeric, linguistic and a hybrid combination thereof;
   (iii) means for selecting a rule for firing based on the determined type of the data;
   (iv) means for obtaining fuzzy membership grades;
   (v) means for aggregating the fuzzy membership grades by invoking a parametric formulation;
   (vi) means for applying a compositional rule of inference parametrically to extract a consequent to obtain a fuzzy output; and
   (vii) means for defuzifying the fuzzy output.

14. The expert system according to claim 13, further comprising means for aggregating the consequents from the fired rules.

15. The expert system according to claim 13, further comprising the means for rearranging a sequence of the data prior to the determining step.

16. The expert system according to claim 13, wherein the data is stored in a database.

17. The expert system according to claim 13, wherein the type of the data is linguistic, and wherein the rule has a singleton consequent.

18. The expert system according to claim 13, wherein the type of the data is hybrid, and wherein the rule has a singleton consequent.

19. An intelligent data management system for reasoning about data, comprising:
   (i) data source for providing the data;
   (ii) means for accessing the data;
   (iii) means for determining a type of the data from a group consisting of numeric, linguistic and a hybrid combination thereof;
   (iv) means for selecting a rule for firing based on the determined type of the data;
   (v) means for obtaining fuzzy membership grades;
   (vi) means for aggregating the fuzzy membership grades by invoking a parametric formulation;
   (vii) means for applying a compositional rule of inference parametrically to extract a consequent to obtain a fuzzy output;
   (viii) means for defuzifying the fuzzy output; and
   (ix) client device for accessing the output.

20. The system according to claim 19, wherein at least one of the client devices is a wireless device.

21. The system according to claim 19, further including a gateway to facilitate wireless access to the system from a wireless client device leveraging existing wireless networks.

22. The system according to claim 19, further including a load balancer for balancing loads between client devices and the system.

23. The system according to claim 19, further including an integrated billing component.

24. A computer program product comprising:
   a memory having microcontroller-readable code embedded therein for reasoning about data using fuzzy logic, comprising:
   (i) code means for accessing the data;
   (ii) code means for determining a type of the data from a group consisting of numeric, linguistic and a hybrid combination thereof;
   (iii) code means for selecting a rule for firing based on the determined type of the data;
   (iv) code means for obtaining fuzzy membership grades;
   (v) code means for aggregating the fuzzy membership grades by invoking a parametric formulation;

(vi) code means for applying a compositional rule of inference parametrically to extract a consequent to obtain a fuzzy output; and (vii) code means for defuzifying the fuzzy output.

25. The computer program product according to claim 24, further comprising code means for aggregating the consequents from the fired rules.

26. The computer program product according to claim 24, further comprising code means for rearranging a sequence of the data prior to the determining step.

27. The computer program product according to claim 24, wherein the data is stored in a database.

28. The method according to claim 1, wherein the parametric formulation ranges between the Formal Logical extreme to the Mamdani extreme.

29. The expert system according to claim 13, wherein the parametric formulation ranges between the Formal Logical extreme to the Mamdani extreme.

30. The system according to claim 19, wherein the parametric formulation ranges between the Formal Logical extreme to the Mamdani extreme.

31. The computer program product according to claim 24, wherein the parametric formulation ranges between the Formal Logical extreme to the Mamdani extreme.

\* \* \* \* \*